(12) United States Patent
Lee et al.

(10) Patent No.: US 7,422,727 B2
(45) Date of Patent: Sep. 9, 2008

(54) APPARATUS FOR PREPARING HYDRAZO-DICARBONAMIDE USING UREA AS STARTING MATERIAL

(75) Inventors: Chun-hyuk Lee, Kyunggi-Do (KR); Sang-Jin Han, Kyunggi-Do (KR)

(73) Assignee: J&J Chemical Co., Ltd. (KR)

( * ) Notice: Subject to any disclaimer, the term of this patent is extended or adjusted under 35 U.S.C. 154(b) by 0 days.

(21) Appl. No.: 11/747,596

(22) Filed: May 11, 2007

(65) Prior Publication Data

US 2007/0207072 A1    Sep. 6, 2007

Related U.S. Application Data

(60) Division of application No. 10/829,418, filed on Apr. 21, 2004, now abandoned, which is a continuation of application No. PCT/KR01/01796, filed on Oct. 24, 2001.

(51) Int. Cl.
*B01J 8/04* (2006.01)
*B01J 8/00* (2006.01)
*B01J 10/00* (2006.01)
*C07C 281/00* (2006.01)

(52) U.S. Cl. .................. 422/189; 422/187; 564/34

(58) Field of Classification Search .................. 422/187, 422/189; 564/34
See application file for complete search history.

(56) References Cited

OTHER PUBLICATIONS

Waki, Kunio; Haraguchi, Mitsuaki; Yamashita, Tadataka, The Thermal Decomposition of Hydrazodicarbamide, 1974, Nippon Kagaku Kaishi, 9, 1668-1672.*

* cited by examiner

*Primary Examiner*—Walter D. Griffin
*Assistant Examiner*—Natasha Young
(74) *Attorney, Agent, or Firm*—Tuchman & Park LLC

(57) ABSTRACT

The present invention relates to a method and apparatus for preparing hydrazodicarbonamide using urea as starting material economically and environmentally desirably. The apparatus includes a pyrolysis furnace to obtain biuret and ammonia by pyrolyzing urea; a recrystallization reactor to purify the biuret obtained from the pyrolysis furnace; a first reactor to obtain an metal monohalobiuret salt by reacting the biuret with metal hypohalogen compound or with halogen and base; a second reactor to synthesize the hydrazodicarbonamide by reacting the monohalobiuret metal salt with ammonia; and an ammonia evaporator to separate the excess ammonia from hydrazodicarbonamide and to supply the separated ammonia to an ammonia concentrator.

3 Claims, 1 Drawing Sheet

APPARATUS FOR PREPARING HYDRAZO-DICARBONAMIDE USING UREA AS STARTING MATERIAL

REFERENCE TO RELATED APPLICATIONS

This application is a divisional of Application Ser. No. 10/829,418 filed Apr. 21, 2004, now abandoned, which is a continuation of PCT/KR01/01796 filed Oct. 24, 2001, which designates the United States.

FIELD OF THE INVENTION

The present invention relates to a method and apparatus for preparing hydrazodicarbonamide with urea as a starting material, and more particularly to a method and apparatus for preparing hydrazodicarbonamide economically and environmentally desirably by producing biuret with urea, and reacting the obtained biuret with ammonia produced during the process of biuret synthesis.

BACKGROUND OF THE INVENTION

Hydrazodicarbonamide(HDCA) is a useful compound as a raw material for preparing azodicarbonamide which is widely used as a foaming agent. As shown in the following reaction Equation 1, azodicarbonamide(2) can be obtained by oxidation of hydrazodicarbonamide (1) with proper oxidation agent.

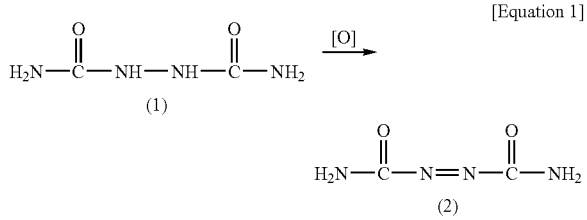

[Equation 1]

The conventional methods for preparing the hydrazodicarbonamide includes methods of (i) using hydrazine as a starting material, (ii) direct synthesis from urea, (iii) obtaining semicarbazide using urea, and then converting the obtained semicarbazide to hydrazodicarbonamide, and (iv) using biuret as starting material.

In the method of using hydrazine as a starting material (Reaction Equation 2), hydrazodicarbonamide is produced by reacting 1 mol of hydrazine(3) with 2 mol of urea(4),

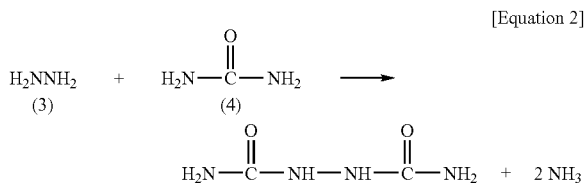

[Equation 2]

The above-identified reaction has a merit in that the process is simple, but it has drawbacks in that the starting material, hydrazine is difficult to synthesis and expensive. The representative methods for preparing hydrazine includes Raschig process and method of using ketazine. However, there are also some problems in that hydrazine obtained by these methods needs concentration process and hydrolysis process. Therefore, the costs for energy and for utility are too high and accordingly the production cost is increasing. Further, hydrazine can also be prepared by the urea process which reacts urea with sodium hypochlorite and sodium hydroxide. But, this method needs excess of sodium hydroxide, and the cost to remove sodium carbonate by-product is very high, and many chemicals are required to remove the by-product. Thus, this method is esteemed as uneconomical and environmentally undesirable.

Following Equation 3 represents the direct synthetic method of hydrazodicarbonamide using urea. As shown in the Equation 3, the reaction of 3 mol of urea with 4 mol of sodium hydroxide and 1 mol of chlorine produces 1 mol of hydrazodicarbonamide. But, this method also is improper because the production cost is high due to the requirement of excess reagents and the process is very complicated. And there is another important problem in that a lot of ammonia are formed as by-product, which is environmentally undesirable.

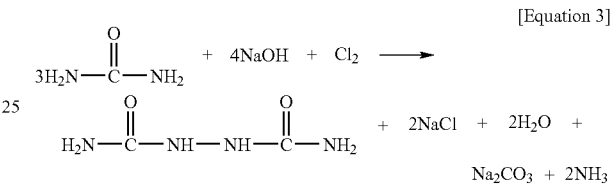

[Equation 3]

Following Equation 4 shows another method of synthesizing hydrazodicarbonamide. The method comprises the steps of obtaining semicarbazide using urea, and subsequently converting the obtained semicarbazide to hydrazodicarbonamide. As shown in Equation 4, sodium monochlorourea salt is obtained by the reaction of urea with sodium hypochlorite, and the sodium monochlorourea salt reacts with excess ammonia in the presence of catalyst to produce the intermediate (semicarbazide), and then the obtained semicarbazide reacts with urea to produce the final product (hydrazodicarbonamide).

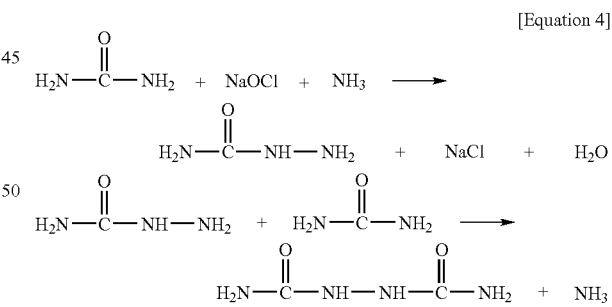

[Equation 4]

However this reaction also is economically inefficient because the reaction needs more than 500 times of excess ammonia per sodium monochlorourea salt, or semicarbazide is obtained by using expensive catalyst. There's another problem that entire process becomes longer because additional reaction of converting semicarbazide to hydrazodicarbonamide should be followed.

Following Equation 5 shows the method of synthesizing hydrazodicarbonamide using biuret (International Application PCT/KR00/00180). It comprises the steps of obtaining metal monohalobiuret salt by reacting biuret with metal hypohalogen (MOX), and subsequently reacting the obtained metal monohalobiuret with ammonia to obtain hydrazodicarbonamide.

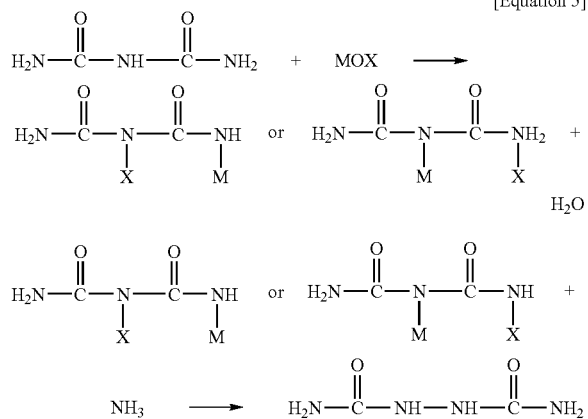

[Equation 5]

However, the above method of producing hydrazodicarbonamide using biuret as a starting material has problems in that the whole process is uneconomic and environmentally undesirable because the biuret used as the starting material is very expensive or it contains a lot of impurities, and the reaction of biuret with ammonia to synthesize hydrazodicarbonamide needs additional ammonia.

SUMMARY OF THE INVENTION

It is an object of the present invention to provide a method for preparing hydrazodicarbonamide economically and environmentally desirably using urea which is cheep and easily acquirable as a starting material.

It is a further object of the present invention to provide a method and apparatus for preparing hydrazodicarbonamide which can minimize the amount of the by-products and starting materials.

It is a further object of the present invention to provide a method and apparatus for preparing hydrazodicarbonamide with high yield by performing the whole process in a continuous manner.

To achieve these objects, the present invention provides a method for preparing hydrazodicarbonamide which comprises the steps of obtaining biuret of Formula 1 and ammonia by pyrolyzing urea, obtaining metal monohalobiuret salt of Formula 2 or 3 by reacting the obtained biuret with metal hypohalogen compound or with halogen and base, and reacting the obtained metal monohalobiuret salt with ammonia.

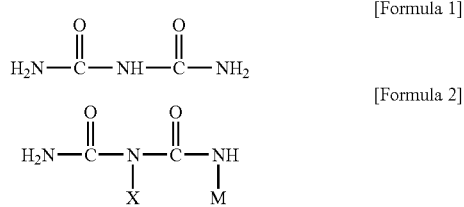

[Formula 1]

[Formula 2]

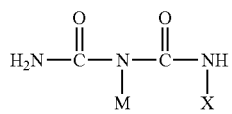

[Formula 3]

In above Formula 2 and 3, M represents metal and X represents halogen. Preferably, the urea pyrolysis temperature is 100~300° C., and the pyrolysis process is carried out while removing ammonia, and the removed ammonia reacts with the metal monohalobiuret salt.

The present invention further provides an apparatus for preparing hydrazodicarbonamide which includes pyrolysis furnace to obtain biuret and ammonia by pyrolyzing urea; recrystallization reactor to purify the biuret obtained from the pyrolysis furnace; a first reactor to obtain an metal monohalobiuret salt by reacting the biuret with metal hypohalogen compound or with halogen and base; a second reactor to synthesize the hydrazodicarbonamide by reacting the metal monohalobiuret salt with ammonia; and an ammonia evaporator to separate the excess ammonia from hydrazodicarbonamide and to forward the separated ammonia to ammonia concentrator.

Preferably, the ammonia concentrator is to concentrate the excess ammonia and ammonia obtained from the pyrolysis furnace, and to supply the concentrated ammonia to the second reactor. The pyrolysis furnace may include a gas injector for injecting inert gas, which does not react with isocyanic acid, into the pyrolysis furnace, and may include means for lowering pressure to remove ammonia from the pyrolysis furnace.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing, wherein.

DETAILED DESCRIPTION OF THE INVENTION

Figure 1:
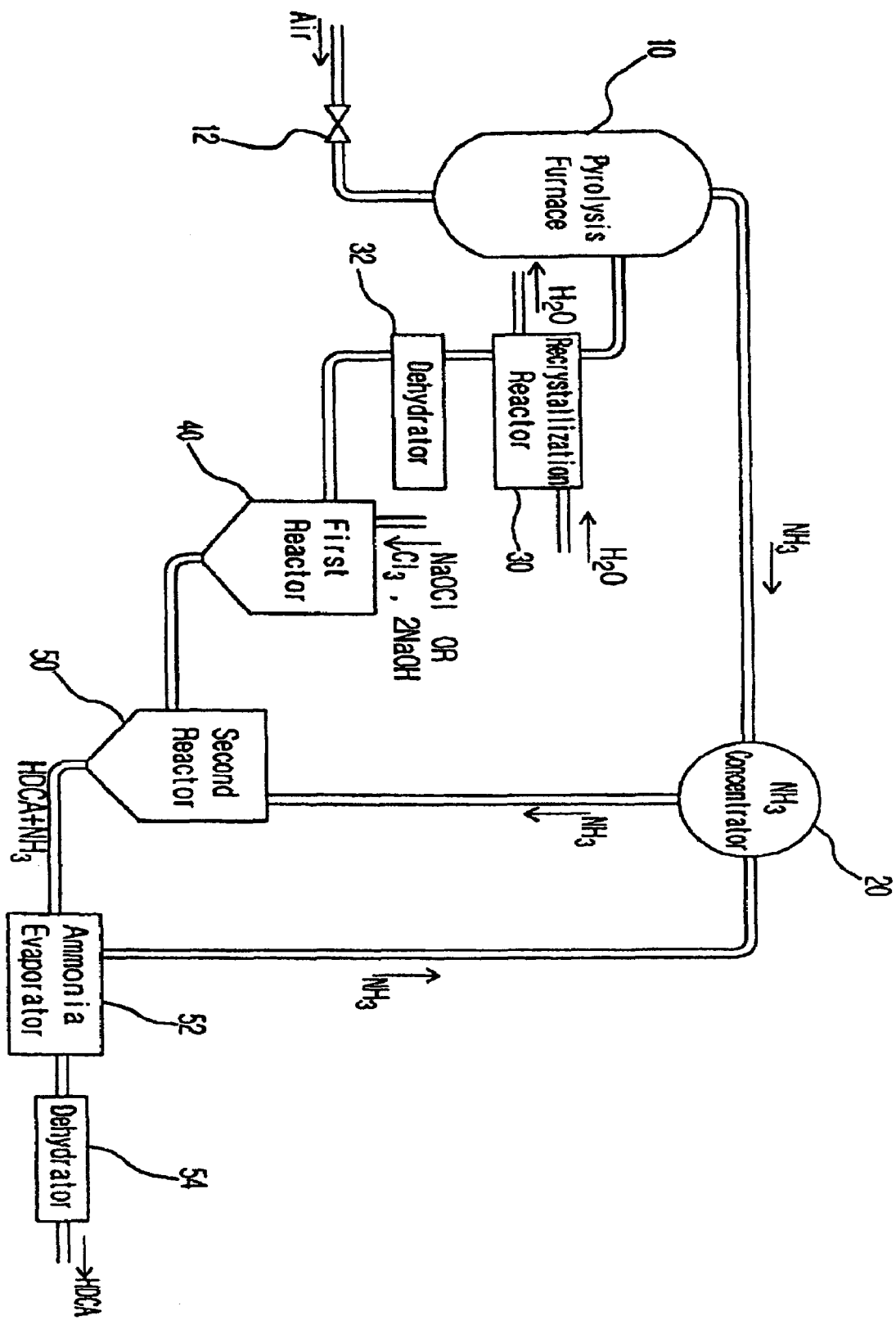
FIG. 1 is a schematic diagram showing an apparatus to prepare hydrazodicarbonamide according to an embodiment of the present invention.

The present invention will become more clearly understood from the following detailed description with reference to the accompanying drawing.

To prepare hydrazodicarbonamide according to the present invention, at first, biuret represented by Formula 1 and ammonia are produced by pyrolyzing urea at a temperature above the melting point of urea. Generally biuret is widely used as a precursor of pharmaceuticals, weedicide and reagent for analysis, also used in large amount as feed for ruminants, and is applied in various field of plastic resins. Furthermore, it is reported that the some derivatives of biuret works as physiological healing agent or chemical therapeutic agent. The following Equation 6 shows the biuret synthesis process by pyrolyzing urea.

[Equation 6]

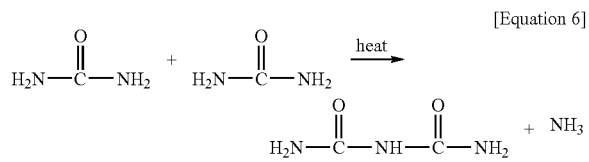

As shown in Equation 6, pyrolysis of 2 mol of urea gives biuret by elimination of ammonia. More precisely, as shown in the following Equation 7, it is presumed that isocyanic acid and ammonia is formed by pyrolysis of urea at first, and then the isocyanic acid reacts with another urea, which gives the target product biuret.

[Equation 7]

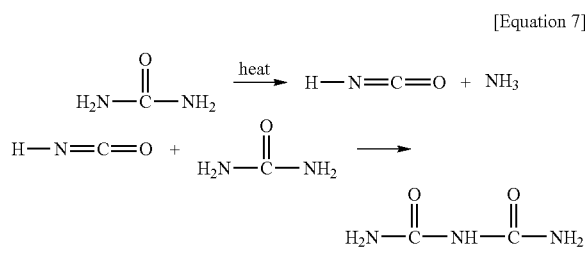

The biuret synthesis by pyrolysis of urea has merits in that the reaction is simple and operation of reaction process is easy, but also has drawbacks in that the conversion ratio of urea to biuret is low because many impurities like triuret, cyanuric acid are formed due to reaction of biuret with isocyanic acid in the biuret formation process. If the temperature is increased and the reaction time is lengthened to increase the conversion ratio, the impurities like triuret, cyanuric acid also increase. If the temperature is lowered to reduce the impurities, the reaction rate will be very slow, which makes the process non-economical. In the present invention, to raise the yield of biuret and to reduce the impurities, the temperature is preferably maintained at 100~300° C. and more preferably is maintained at 130~170° C.

Further, if inert gas such as air and nitrogen which does not react with isocyanic acid is injected into the reactor, and/or the pressure of reactor is lowered, the ammonia, the byproduct formed during the reaction, can be effectively removed from the reactor. Then the reaction rate increases, and formation of impurities can be lowered, too. In addition, liquid phase organic compound which can be changed to the inert gas in the reactor of high temperature can be used as the inert gas source.

Further, if necessary, catalyst to increase the pyrolysis reaction rate can be used. Preferably, inorganic acid catalyst such as nitric acid, hydrochloric acid, and sulfuric acid, and acid type catalyst such as thionyl chloride, and phosphorous containing substances such as sodium phosphate can be used as the catalyst. The preferable amount of catalyst is 0.001~0.5 mol per 1 mol of urea, and more preferable amount is 0.01~0.3 mol per 1 mol of urea.

Metal monohalobiuret salt of the following Formula 2 or 3 can be produced by reacting the obtained biuret with metal hypohalogen compound or halogen and base.

[Formula 2]

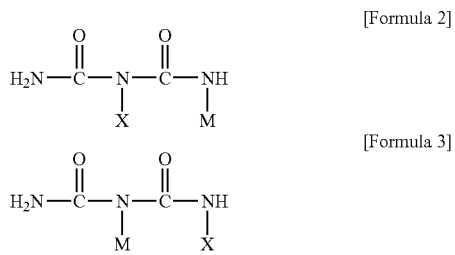

[Formula 3]

In above Formula 2 and 3, M represents metal and X represents halogen. The direct method of preparing metal monohalobiuret salt by reacting biuret with metal hypohalogen compound is shown in Equation 8, and the specific example is shown in Equation 9.

[Equation 8]

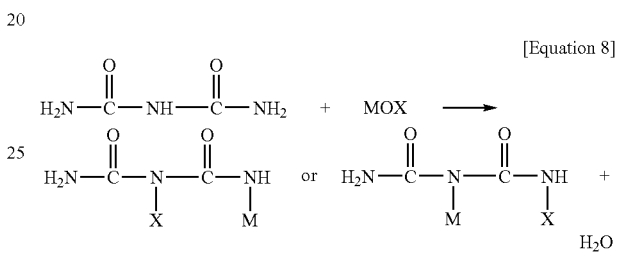

In above Equation, M represent metal and X represent halogen.

[Equation 9]

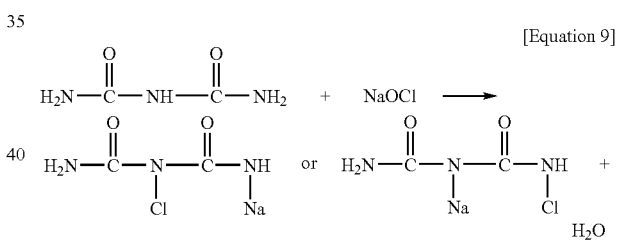

Referring the above Equation 9, biuret reacts with sodium hypochlorite to form sodium chlorobiuret salt. Because above reaction is exothermic, the reaction system preferably would be maintained at low temperature. But the obtained sodium chlorobiuret salt is stable against moderate heat, it can be prepared at room temperature. Preferable reaction temperature is less than 60° C., and more preferably −10~60° C. and most preferably −5~35° C. Considering the economic efficiency and operational facility, the reaction mol ratio of metal hypohalogen per 1 mole of urea is preferably between 0.1 and 2. When the reaction mol ratio is less than 1 mol, the excess biuret can be recovered and can be reused. In above reaction, when the reaction mol ratio is less than 0.1 or the reaction temperature is less than −10° C., the reaction time would be too long. And if the reaction mol ratio is more than 2, the production cost increases and the side reaction may occur. Moreover, if the reaction temperature is more than 60° C., the produced metal monohalobiuret salt can be decomposed because it is unstable at high temperature. The sodium chlorobiuret salt obtained under above-mentioned condition can be used directly or can be stored for next reaction.

A process of producing metal monohalobiuret salt of above Formula 2 or 3 by reacting biuret with halogen and base is shown in Equation 10. As shown in Equation 10, after reacting biuret with halogen such as chlorine or halogen compound to obtain monohalobiuret(5), metal monohalobiuret salt can be obtained by adding base such as metal hydroxide (for example, sodium hydroxide, potassium hydroxide, calcium hydroxide) to the obtained monohalobiuret(5).

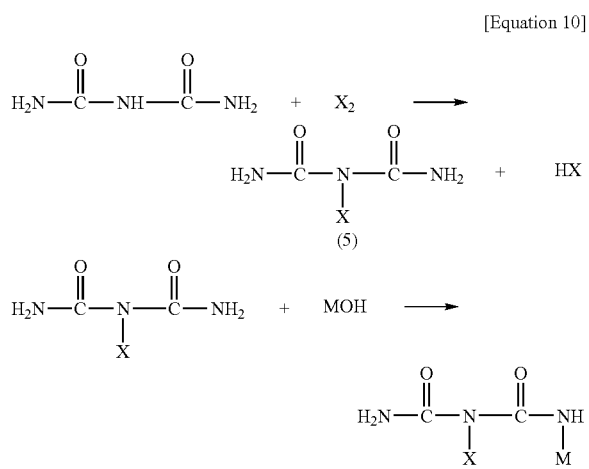

[Equation 10]

In above Equation 10, M represent metal and X represent halogen.

Considering that the reaction for obtaining monohalobiuret(5) is exothermic, it would be advantageous that the reaction temperature is maintained lower, specifically less than 60° C., preferably −10~60° C. and most preferably −5~30° C. for the proper reaction rate and the stability of reaction. Alternatively, metal monohalobiuret salt can be obtained by mixing metal hydroxide with biuret at first, and then reacting halogen with the obtained product. Because this reaction is also exothermic, the reaction temperature should be maintained lower, specifically to −10~60° C. and more preferably −5~30° C. In above reaction, when the reaction temperature is less than 10° C., the reaction time would be too long, and when the reaction temperature is more than 60° C., the metal monohalobiuret salt can be decomposed because it is unstable against heat. As shown in Equation 11, the obtained metal monohalobiuret salt can be metal 3-monohalobiuret salt(6) or metal 1-monohalobiuret salt(7).

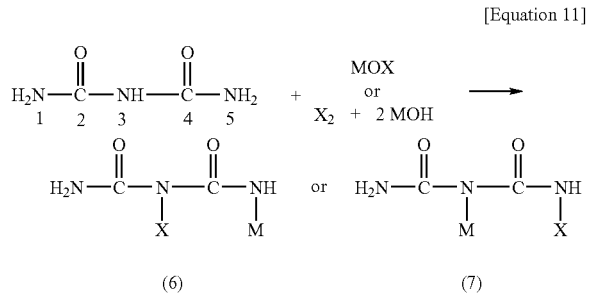

[Equation 11]

To produce hydrazodicarbonamide, the obtained metal monohalobiuret salt reacts with ammonia which is formed while pyrolyzing the urea. The reaction mechanism is presumed to be similar to Favorskii reaction shown in Equation 12 or to Hoffman rearrangement reaction in Equation 13.

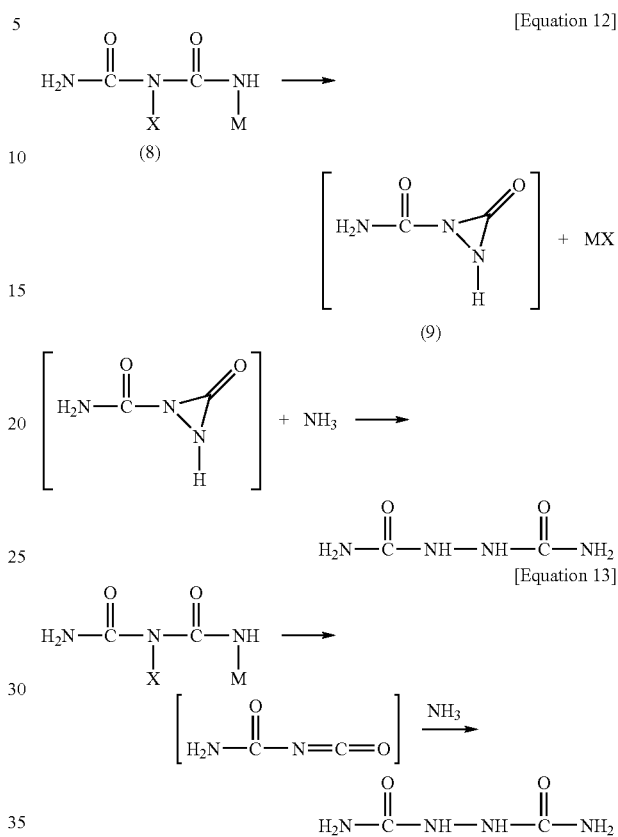

[Equation 12]

[Equation 13]

Referring the above Equation 12, by the inter-molecular reaction of anionic nitrogen atoms in metal monohalobiuret salt (8), unstable diaziridinone derivative (9) is formed by formation of nitrogen-nitrogen bond while metal halogen compound being eliminated. The diaziridinone derivative (9) readily reacts with highly reactive ammonia, and the hydrazodicarbonamide is prepared. Furthermore, referring the above Equation 13, it is presumed that metal monohalobiuret salt is converted to the compound which contains isocyanate group, and the converted isocyanate compound react with highly reactive ammonia to form hydrazodicarbonamide.

In the reaction of metal monohalobiuret salt with ammonia which is by-product of urea pyrolysis, considering the reaction rate and efficiency, preferable reaction temperature is between 0 and 150° C., more preferably between 30 and 150° C. When the reaction temperature is less than 0° C., the reaction rate is too slow and the economically inefficient, and when above reaction temperature is more than 150° C., the equipment cost is increase because the equipment must be designed to endure the internal pressure caused by ammonia vaporization.

Furthermore, ammonia can be used in either form of gaseous ammonia, or liquid ammonia or ammonium hydrate. Ammonia can be preferably used with excess amount to increase the reaction rate. The amount of ammonia can be between 1 and 1000 mol per 1 mol of metal monohalobiuret salt, more preferably is between 2 and 500 mol, most preferably between 5 and 100 mol. The excess ammonia except 1 mol of ammonia which react with 1 mol of metal monohalobiuret salt can be recovered and reused for next reaction.

When the reaction temperature is high while using large amount of ammonia, the pressure of the reaction system can be raised to prevent the vaporization of ammonia. This improves the reaction rate and efficiency, and the preferable range of the pressure is between 1 and 100 kgf/cm².

According to the present invention, high yield can be achieved without using catalyst. However, if catalyst is used, it is very useful because the reaction time can be shortened, and the reaction efficiency can be improved. The examples of the catalyst includes at least one compound selected from the group consisting of sulfuric acid salt, chloride salt, carbonate salt or hydroxide salt of basic metal or amphoteric metal, and organic compounds including the metals. The preferable amount of the catalyst is between 0.001 and 1 mol, more preferably is 0.01~0.5 mol per 1 mol of metal monohalobiuret salt. As the catalyst, inorganic acid such as sulfuric acid, hydrochloric acid, or nitric acid can be added with the amount of 0.05~3.0 mol per 1 mol of metal monohalobiuret salt.

As a solvent of the reactant(biuret) or of entire reaction system, water can be used. If necessary, as a second solvent, at least one solvent selected from the group consisted with the polar solvent such as methanol, ethanol, propanol, isopropanol, tetrahydrofuran, acetonitrile, and the aprotic solvent such as dimethylformamide, dimethylsulfoxide, dimethylacetamide can be added. The amount of the second solvent is not limited particularly, but the preferable amount is between 0.1 and 50 times to the total weight of water, more preferable amount is 0.2~3.0. Furthermore, the second solvent can be introduced at the start of the reaction as a solvent for biuret or after mixing biuret solution with sodium hypochlorite solution.

The reaction for preparing hydrazodicarbonamide using urea as a starting material according to the present invention is shown in Equation 14 as a whole. In addition, an apparatus for preparing hydrazodicarbonamide according to an embodiment of the present invention is shown in FIG. 1.

[Equation 14]

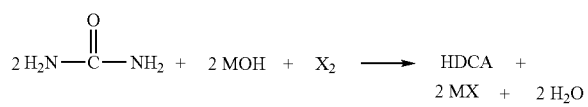

As shown in FIG. 1, an apparatus to prepare hydrazodicarbonamide according to an embodiment of the present invention comprises pyrolysis furnace 10 to obtain biuret and gaseous ammonia by pyrolyzing urea. The pyrolysis furnace 10 preferably includes a gas injector 12 for injecting inert gas into the pyrolysis furnace 10, or may includes means (not shown) for lowering pressure of the furnace 10 to easily remove ammonia from the pyrolysis furnace 10. The non-limiting examples of the inert gas includes air, nitrogen, and liquid phase organic compound which changes into an inert gas in the pyrolysis furnace 10, which does not react with isocyanic acid.

Ammonia removed from said pyrolysis furnace 10 is preferably supplied to ammonia concentrator 20, and the function of the ammonia concentrator 20 is concentrating the ammonia supplied from the pyrolysis furnace 10 and the excess ammonia remained after formation of hydrazodicarbonamide. The impurities, such as cyanuric acid and triuret, in biuret produced in the pyrolysis furnace 10 is separated by recrystallization means comprising recrystallization reactor 30 and dehydrator 32 such as a centrifuger, and then supplied to the first reactor 40.

Purified biuret which is sent to the first reactor 40 reacts with metal hypohalogen compound (for example, NaOCl) or halogen (for example, chlorine) and base to produce metal monohalobiuret salt, and then the produced metal monohalobiuret salt is supplied to the second reactor 50. The metal monohalobiuret salt reacts with ammonia to produce hydrazodicarbonamide, and the ammonia is preferably supplied from the ammonia concentrator 20. The obtained hydrazodicarbonamide and excess ammonia are supplied to the ammonia evaporator 52. Ammonia evaporator 52 vaporizes the excess ammonia, and the vaporized ammonia is supplied to ammonia concentrator 20. The hydrazodicarbonamide separated from the excess ammonia is purified by dehydrator 54 such as filter.

As shown in Equation 13 and FIG. 1, according to the present invention, the hydrazodicarbonamide can be prepared in one continuous process from a starting material, urea. Because the entire process is carried out continuously, the efficiency of process can be improved. In addition, the production cost can be lowered by greatly reducing the required amount of the raw material due to the fact that metal monohalobiuret salt reacts with ammonia, which is produced as a byproduct in the process of biuret formation. Thus, hydrazodicarbonamide can be prepared environmentally desirably by using the environmentally undesirable by-product ammonia.

Hereinafter, the preferable examples and manufacturing examples are provided for better understanding of the present invention. However, the present invention should not be understood to be restricted to the following Examples.

MANUFACTURING EXAMPLES 1 to 4

Preparation of Biuret

A four necked round bottomed flask was charged with 500 g (8.33 mole) of urea, stirred vigorously, and air was injected to the bottom side of the flask at the rate shown in following table 1. Simultaneously the reaction was carried out during 5 hours with the reaction temperature maintained at 140° C. by heating. After completion of reaction, the composition of the obtained solid was analyzed by using liquid chromatography and the result was disclosed by following Table 1.

TABLE 1

| Example | Air injection rate (L/min) | Content of Urea (wt %) | Content of Biuret (wt %) | Content of Cyanuric acid and other solid (wt %) |
|---|---|---|---|---|
| 1 | 0 | 62 | 35 | 3 |
| 2 | 1 | 41 | 55 | 4 |
| 3 | 2 | 38 | 60 | 2 |
| 4 | 4 | 37 | 61 | 2 |

MANUFACTURING EXAMPLES 5 to 7

Preparation of Biuret

Biuret was prepared by the same method as Example 1 except that the reaction was carried out for 3 hours while varying the reaction temperature and maintaining the air injection rate at 2 L/min. After completion of reaction, the composition of the obtained solid is analyzed by using liquid chromatography and the result was disclosed by following Table 2.

TABLE 2

| Example | The reaction temperature (° C.) | Content of Urea (wt %) | Content of Biuret (wt %) | Content of Cyanuric acid and other solid (wt %) |
|---|---|---|---|---|
| 4 | 150 | 47 | 50 | 3 |
| 5 | 160 | 38.5 | 57 | 4.3 |
| 6 | 170 | 28 | 65 | 7 |

MANUFACTURING EXAMPLES 8 to 10

Preparation of Biuret

Biuret was prepared by the same method as Example 1 except that the reaction was carried out with lowering the pressure as shown in following Table 3 by vacuum pump instead of air injection. After completion of reaction, the composition of the obtained solid is analyzed by using liquid chromatography and the result was disclosed by the following Table 3.

TABLE 3

| Example | The pressure (mmHg) | Content of Urea (wt %) | Content of Biuret (wt %) | Content of Cyanuric acid and other solid (wt %) |
|---|---|---|---|---|
| 8 | 380 | 56 | 50 | 4 |
| 9 | 190 | 41.5 | 55 | 3.5 |
| 10 | 100 | 40 | 57 | 3 |

MANUFACTURING EXAMPLES 11 to 13

Preparation of Biuret

Biuret was prepared by the same method as Example 1 except that the reaction was carried out using 0.05 mole of various catalysts per 1 mole of urea, and the air injection rate is fixed at 2 L/min. After completion of reaction, the composition of the obtained solid is analyzed by using liquid chromatography and the result was disclosed by following Table 4.

TABLE 4

| Example | Catalyst | Content of Urea (wt %) | Content of Biuret (wt %) | Content of Cyanuric acid and other solid (wt %) |
|---|---|---|---|---|
| 11 | Sulfuric acid | 34 | 62 | 4 |
| 12 | Sodium phosphate | 36 | 61 | 3 |
| 13 | Thionyl chloride | 35 | 62 | 3 |

MANUFACTURING EXAMPLE 14

Synthesis of Sodium Chlorobiuret Salt

A 2 L glass reactor was charged with 423.1 g (0.287 mole) of slurry solution of 7% biuret, and cooled to 5° C. with stirring. To this reactor, aqueous solution of 12% sodium hypochlorite was added, and the reaction temperature of the system was maintained below 5° C. After completion of addition, the reaction solution was analyzed by iodometry and by using liquid chromatography. The available chlorine was 3.37%. This corresponded to a yield of 98%.

MANUFACTURING EXAMPLE 15

Synthesis of Sodium Chlorobiuret Salt

A 2 L glass reactor was charged with 423.1 g (0.287 mole) of slurry solution of 7% biuret, and cooled to 5° C. with stirring. To this reactor, 223 g (0.575 mole) of aqueous solution of 10.3% sodium hydroxide was added, and 20.3 g (0.287 mole) of gaseous chlorine was added maintaining the reaction temperature of the system below 10° C. After completion of the addition, the reaction solution was analyzed by iodometry and by using liquid chromatography. The available chlorine was 3.0%. This corresponded to a yield of 98%.

MANUFACTURING EXAMPLE 16

Synthesis of Sodium Chlorobiuret Salt

A 2 L glass reactor was charged with 423.1 g (0.287 mole) of slurry solution of 7% biuret, and cooled to 5° C. with stirring. To this reactor, 20.3 g (0.287 mole) of gaseous chlorine was added maintaining the reaction temperature of the system below 10° C. After addition of gaseous chlorine, 223 g (0.575 mole) of aqueous solution of 10.3% sodium hydroxide was added while vigorously stirring and the reaction temperature was maintained below 5° C. After completion of addition, the reaction solution was analyzed by iodometry and by using liquid chromatography. The available chlorine was 3.0%. This corresponded to a yield of 98%.

EXAMPLES 1-9

Synthesis of Hydrazodicarbonamide

A 2 L autoclave was charged with 593.1 g of sodium chlorobiuret salt obtained by the above Manufacturing Example 14, and cooled to 10° C. with stirring. Maintaining the reaction temperature of solution below 10° C., 600 g (8.8 mole) of 25% aqueous ammonia solution was added to this while vigorously stirring. The reaction was carried out varying the reaction temperature and reaction time. After completion of reaction, unreacted ammonia was removed, and the reaction solution was filtered to get hydrazodicarbonamide insoluble to water and the yield of hydrazodicarbonamide was calculated and closed in Table 5.

TABLE 5

| Example | Reaction condition (temperature, time) | Yield (%) |
|---|---|---|
| 1 | 30° C., 1 hr | 85 |
| 2 | 30° C., 2 hrs | 90 |
| 3 | 30° C., 3 hrs | 89 |
| 4 | 60° C., 1 hr | 91 |
| 5 | 60° C., 2 hrs | 89 |
| 6 | 60° C., 3 hrs | 90 |
| 7 | 90° C., 1 hr | 88 |
| 8 | 90° C., 2 hrs | 89 |
| 9 | 90° C., 3 hrs | 90 |

EXAMPLES 10-18

Synthesis of Hydrazodicarbonamide

Reaction was carried out by the same method as Example 4 except that the 0.5 mole of various catalysts shown in Table 6 was added. After completion of reaction, unreacted ammonia was removed, and the reaction solution was filtered to get hydrazodicarbonamide insoluble to water and the yield of hydrazodicarbonamide was calculated and disclosed by the following Table 6.

TABLE 6

| Example | Catalyst used | Yield (%) |
|---|---|---|
| 10 | $ZnCl_2$ | 94 |
| 11 | $Zn(OH)_2$ | 92 |
| 12 | $AlCl_3$ | 90 |
| 13 | $BaCl_2$ | 91 |
| 14 | $CdCl_2$ | 92 |
| 15 | $ZnSO_4$ | 93 |
| 16 | $ZnCl_2 + AlCl_3$ (0.025 mole each) | 96 |
| 17 | $ZnCl_2 + BaCl_2$ (0.025 mole each) | 94 |
| 18 | $ZnCl_2 + CdCl_2$ (0.025 mole each) | 96 |

EXAMPLES 19-27

Synthesis of Hydrazodicarbonamide

A 2 L autoclave was charged with 593.1 g of sodium chlorobiuret salt obtained by the manufacturing Example 15, and cooled to 10° C. with stirring. Maintaining the reaction temperature of solution below 10° C. 600 g (8.8 mole) of 25% aqueous ammonia solution was added while vigorously stirring. The reaction was carried out varying the reaction temperature and reaction time. After completion of reaction, unreacted ammonia was removed, and the reaction solution was filtered to get hydrazodicarbonamide insoluble to water and the yield of hydrazodicarbonamide was calculated and disclosed by the following Table 7.

TABLE 7

| Example | Reaction condition (temperature, time) | Yield (%) |
|---|---|---|
| 19 | 30° C., 1 hr | 78 |
| 20 | 30° C., 2 hrs | 89 |
| 21 | 30° C., 3 hrs | 89 |
| 22 | 60° C., 1 hr | 88 |
| 23 | 60° C., 2 hrs | 90 |
| 24 | 60° C., 3 hrs | 90 |
| 25 | 90° C., 1 hr | 87 |
| 26 | 90° C., 2 hrs | 86 |
| 27 | 90° C., 3 hrs | 89 |

EXAMPLES 28-36

Synthesis of Hydrazodicarbonamide

Reaction was carried out by the same method as Example 22 except that the 0.05 mole of various catalysts shown by following table 8 was added. After completion of reaction, unreacted ammonia was removed, and the reaction solution was filtered to get hydrazodicarbonamide insoluble to water and the yield of hydrazodicarbonamide was calculated and disclosed by the following Table 8.

TABLE 8

| Example | Used catalyst | Yield (%) |
|---|---|---|
| 28 | $ZnCl_2$ | 94 |
| 29 | $Zn(OH)_2$ | 91 |
| 30 | $AlCl_3$ | 89 |
| 31 | $BaCl_2$ | 91 |
| 32 | $CdCl_2$ | 93 |
| 33 | $ZnSO_4$ | 92 |
| 34 | $ZnCl_2 + AlCl_3$ (0.025 mole each) | 97 |
| 35 | $ZnCl_2 + BaCl_2$ (0.025 mole each) | 93 |
| 36 | $ZnCl_2 + CdCl_2$ (0.025 mole each) | 96 |

EXAMPLES 37-45

Synthesis of Hydrazodicarbonamide

A 2 L autoclave was charged with 593.1 g of sodium chlorobiuret salt obtained by the above Manufacturing Example 16, and cooled to 10° C. with stirring. Maintaining the reaction temperature of solution below 10° C. 600 g (8.8 mole) of 25% aqueous ammonia solution was added while vigorously stirring. The reaction was carried out varying the reaction temperature and reaction time. After completion of reaction, unreacted ammonia was removed, and the reaction solution was filtered to get hydrazodicarbonamide insoluble to water and the yield of hydrazodicarbonamide was calculated and disclosed by the following Table 9.

TABLE 9

| Example | Reaction condition (temperature, time) | Yield (%) |
|---|---|---|
| 37 | 30° C., 1 hr | 79 |
| 38 | 30° C., 2 hrs | 88 |
| 39 | 30° C., 3 hrs | 89 |
| 40 | 60° C., 1 hr | 89 |
| 41 | 60° C., 2 hrs | 90 |
| 42 | 60° C., 3 hrs | 91 |
| 43 | 90° C., 1 hr | 88 |
| 44 | 90° C., 2 hrs | 88 |
| 45 | 90° C., 3 hrs | 89 |

EXAMPLES 46-54

Synthesis of hydrazodicarbonamide

Reaction was carried out by the same method as Example 40 except that the 0.05 mole of various catalysts shown by following Table 10 was added. After completion of reaction, unreacted ammonia was removed, and the reaction solution was filtered to get hydrazodicarbonamide insoluble to water and the yield of hydrazodicarbonamide was calculated and disclosed by the following Table 10.

TABLE 10

| Example | Used catalyst | Yield (%) |
|---|---|---|
| 46 | $ZnCl_2$ | 93 |
| 47 | $Zn(OH)_2$ | 90 |
| 48 | $AlCl_3$ | 90 |
| 49 | $BaCl_2$ | 90 |
| 50 | $CdCl_2$ | 92 |
| 51 | $ZnSO_4$ | 89 |
| 52 | $ZnCl_2 + AlCl_3$ (0.025 mole each) | 95 |

TABLE 10-continued

| Example | Used catalyst | Yield (%) |
|---|---|---|
| 53 | ZnCl$_2$ + BaCl$_2$ (0.025 mole each) | 93 |
| 54 | ZnCl$_2$ + CdCl$_2$ (0.025 mole each) | 94 |

EXAMPLES 55-58

Synthesis of Hydrazodicarbonamide

A 2 L autoclave was charged with 593.1 g of sodium chlorobiuret salt obtained by the above Manufacturing Example 14, and cooled to 10° C. with stirring. Maintaining the reaction temperature of solution below 10° C., aqueous ammonia solution was added while vigorously stirring for an hour at the amount shown by the following Table 11. After completion of reaction, unreacted ammonia was removed, and the reaction solution was filtered to get hydrazodicarbonamide insoluble to water and the yield of hydrazodicarbonamide was calculated and disclosed by the following table 11.

TABLE 11

| Example | Mole ratio of ammonia vs sodium chlorobiuret salt (%) | Yield (%) |
|---|---|---|
| 55 | 15 | 75 |
| 56 | 30 | 87 |
| 57 | 60 | 90 |
| 58 | 90 | 89 |

EXAMPLES 59-62

Synthesis of Hydrazodicarbonamide

A 2 L autoclave was charged with 593.1 g of sodium chlorobiuret salt obtained by the above Manufacturing Example 14, and cooled to 10° C. with stirring and various organic solvent shown in Table 12 was added at the amount of 0.5 times to weight of water. Maintaining the reaction temperature of solution below 10° C., 600 g of 25% aqueous ammonia solution was added while vigorously stirring for an hour. After completion of reaction, unreacted ammonia was removed, and the reaction solution was filtered to get hydrazodicarbonamide insoluble to water and the yield of hydrazodicarbonamide was calculated and disclosed by the following Table 12.

TABLE 12

| Example | Solvent used | Yield (%) |
|---|---|---|
| 59 | Methanol | 90 |
| 60 | Dimethylformamide | 94 |
| 61 | Tetrahydrofuran | 90 |
| 62 | Acetonitrile | 88 |

As described above, with the method and apparatus for preparing hydrazodicarbonamide according to the present invention, hydrazodicarbonamide can be synthesized from cheep and easily available urea as a starting material. In addition, hydrazodicarbonamide can be prepared economically and environmentally desirably due to the minimization of byproduct and input raw material, and with high efficiency from continuous process.

What is claimed is:

1. An apparatus for preparing hydrazodicarbonamide comprising:
   a pyrolysis furnace to obtain biuret and ammonia by pyrolyzing urea;
   a recrystallization reactor to purify the biuret obtained from the pyrolysis furnace;
   a first reactor to obtain an metal monohalobiuret salt by reacting the biuret with metal hypohalogen compound or with halogen and base;
   a second reactor to synthesize the hydrazodicarbonamide by reacting the monohalobiuret metal salt with ammonia; and
   an ammonia evaporator to separate the excess ammonia from hydrazodicarbonamide and to supply the separated ammonia to an ammonia concentrator, wherein wherein the ammonia concentrator is to concentrate the excess ammonia and ammonia obtained at the pyrolysis furnace, and is to supply the concentrated ammonia to the second reactor.

2. The apparatus for preparing hydrazodicarbonamide according to claim 1, wherein the pyrolysis furnace has a gas injector for injecting inert gas, which does not react with isocyanic acid, into the pyrolysis furnace.

3. The apparatus for preparing hydrazodicarbonamide according to claim 1, wherein the pyrolysis furnace has means for lowering pressure to remove the ammonia from the pyrolysis furnace.

* * * * *